United States Patent [19]
Elghazzawi

[11] Patent Number: 5,697,378
[45] Date of Patent: Dec. 16, 1997

[54] METHOD AND APPARATUS FOR USING MULTIPLE LEADS FOR QRS DETECTION

[75] Inventor: Ziad Fawaz Elghazzawi, Medford, Mass.

[73] Assignee: Siemens Medical Systems, Inc., Iselin, N.J.

[21] Appl. No.: 768,093

[22] Filed: Dec. 16, 1996

[51] Int. Cl.$^6$ ................................................. A61B 5/0402
[52] U.S. Cl. ........................... 128/696; 128/901; 128/708
[58] Field of Search ................................. 128/696, 901, 128/702, 703–705, 708, 920

[56] References Cited

U.S. PATENT DOCUMENTS

| | | | |
|---|---|---|---|
| 5,381,803 | 1/1995 | Herleikson et al. | 128/708 |
| 5,421,342 | 6/1995 | Mortara | 128/696 |
| 5,479,933 | 1/1996 | Atarius et al. | 123/696 |
| 5,490,515 | 2/1996 | Mortara | 128/696 |
| 5,564,428 | 10/1996 | Soemmo et al. | 128/696 |
| 5,598,848 | 2/1997 | Swanson et al. | 128/696 |

*Primary Examiner*—William E. Kamm
*Assistant Examiner*—Kennedy J. Schaetzle
*Attorney, Agent, or Firm*—Lawrence C. Edelman

[57] ABSTRACT

A method and apparatus for reducing noise in an output signal produced from a plurality of input signals indicative of a repetitious phenomena exhibited by a signal source. The apparatus comprises: (a) signal receiving means adapted for being coupled to a plurality of sensors positioned with respect to a signal source such that each of the sensors is subjected to a unique representation of a repetitious phenomena exhibited by the signal source, for obtaining from the sensors a plurality of received signals in which noise may be present; (b) signal detecting means for detecting the occurrence of the phenomena in each of the plurality of received signals; (c) signal strength determining means responsive to the plurality of received signals for determining the signal strength of the phenomena in each of the plurality of received signals; and (d) proportional adding means for additively combining the plurality of received signals together for developing a combined signal, with each received signal having a weight in the combined signal which is in direct proportion to the signal strength of the phenomena in that signal as determined by the signal strength determining means, the output signal indicative of the phenomena being developed from the combined signal. In a preferred embodiment the signal detecting means is responsive to the output signal of the proportional adding means.

13 Claims, 2 Drawing Sheets

METHOD AND APPARATUS FOR USING MULTIPLE LEADS FOR QRS DETECTION

BACKGROUND OF THE INVENTION

1. Field of the Invention

The present invention relates to a method and apparatus for producing a reduced noise output signal from a plurality of input signals each having a repetitious phenomena therein. More specifically, the method and apparatus combines the signals from multiple electrocardiogram (ECG) leads for providing a reduced noise output signal from which QRS complexes can be detected with improved accuracy.

2. Description of the Prior Art

Noise reduction is important in a number of signal processing areas, such as electrocardiology, electroencephalography, data transmission, etc. By providing noise reduction, a particular signal can be utilized in a manner such that the undesirable effects of noise are substantially reduced.

For example, in electrocardiography, the QRS complexs are frequently difficult to unambiguously and reliably detect in the plurality of sensed ECG signals due to the presence of noise in the ECG signals. Thus, accurate heart rate (e.g., arrhythmia) monitoring is plagued by false-positive detection of QRS complexes caused by noise of non-cardiac origin. Non-cardiac noise may be generated, for example, by skeletal muscle action. Accurate detection of the repetitious QRS complexes is central to reliable heart rate monitoring.

One type of prior art technique commonly employed to prevent non-cardiac noise from degrading the accuracy of QRS complex detection is lead-switching. That is, the signal-to-noise ratio of each of the ECG signal leads is determined, and those that don't have a signal-to-noise ratio that exceeds a predetermined threshold level, are not used for QRS detection. This technique is somewhat undesirable since even low signal-to-noise ratio ECG signals may still have useful information contained therein. Furthermore, although there are also various arrangements known for filtering ECG signals to reduce noise therein, there still remains a need for providing accurate and unambiguous QRS detection in a more simplified and reliable manner.

SUMMARY OF THE INVENTION

A method and apparatus for reducing noise in an output signal produced from a plurality of input signals indicative of a repetitious phenomena exhibited by a signal source. The method comprises the steps of: (a) obtaining from a plurality of sensors positioned with respect to the signal source so as to be subjected to a unique representation of a repetitious phenomena exhibited by the signal source, a corresponding plurality of received signals in which noise may be present; (b) detecting the occurrence of the phenomena in each of the plurality of received signals; (c) determining the signal strength of the phenomena in each of the plurality of received signals; and (d) additively combining the plurality of received signals together for providing a combined signal, with each received signal having a weight in the combined signal which is in direct proportion to the signal strength of its phenomena as determined by the prior step, with the output signal being developed from said combined signal.

DETAILED DESCRIPTION OF THE PREFERRED EMBODIMENTS

Figure 1:
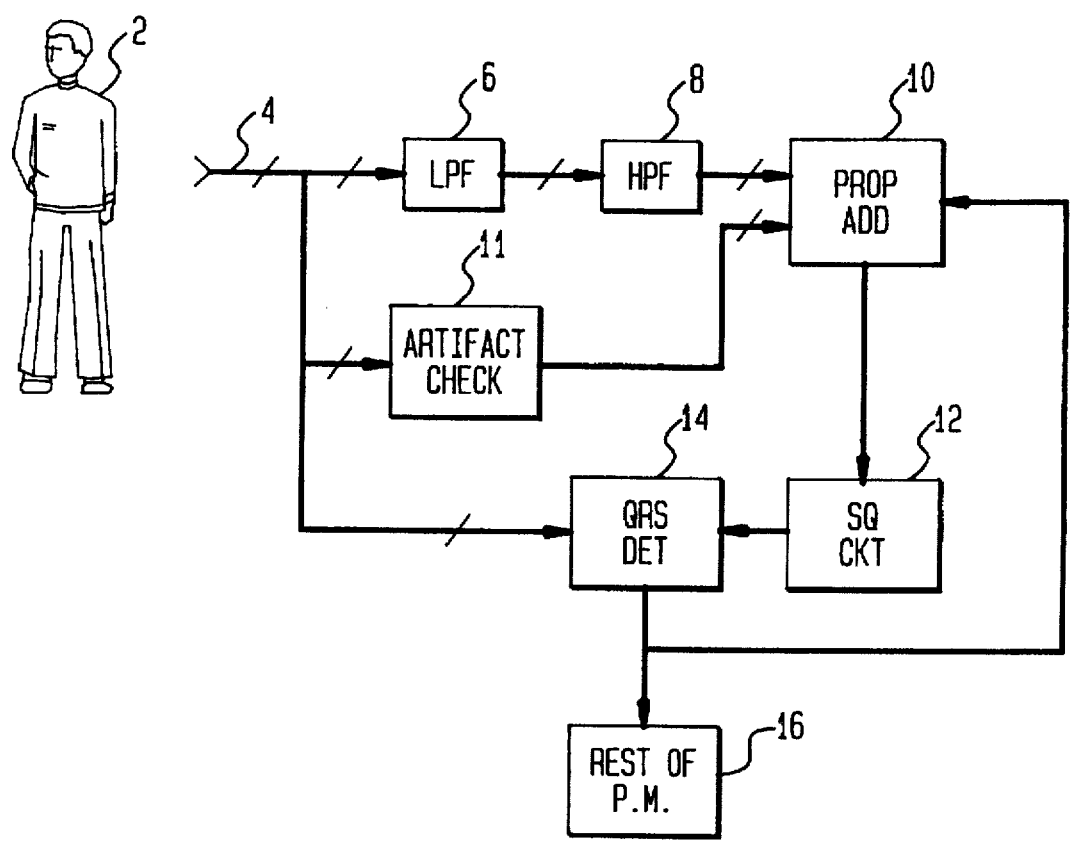
FIG. 1 illustrates in block diagram form a patient monitor constructed in accordance with the principles of the invention.

AS shown in FIG. 1, each of a plurality (e.g., 2–12) physiological (ECG) signal leads 4 are connected to a patient 2 using a respective plurality of sensors (not shown). For detection of QRS complexes on leads 4, each of the leads is first filtered using a low pass filter (LPF) 6, and then filtered using a high pass filter 8. An ECG front end of a type well known and conventional in patient monitors (and therefore not shown), develops electrical signals on leads 4 that are representative of ECG data acquired from the patient. In the illustrated embodiment the frequency range of interest for the QRS complexes is between 5 and 16 Hz, and therefore the cutoff frequency for LPF 6 is 16 Hz, and the corner frequency for HPF 8 is 5 Hz.

In a digital implementation of the illustrated embodiment, HPF 8 may comprise a summation of first and second differencing operations.

The first difference operation (fd) is defined as:

$fd[i]=abs(data[i+3]-data[i-3])$;

the second difference operation (sd) is defined as:

$sd[i]=abs(fd[i+3]-fd[i-3])$; and the total difference (td) output is defined as:

$td[i]=fd[i]+sd[i]$;

where data[i] is the i–th sample of each of the incoming ECG lead signals 4; fd[i] is the absolute value of the i–th sample of the first difference of each of the incoming ECG lead signals 4; sd[i] is the absolute value of the i–th sample of the second difference of each of the incoming ECG lead signals 4; and td[i] is the i–th sample of the absolute value of the total difference that consists of the summation of the absolute value of the first and second differences. "abs" is the absolute value function.

In the illustrated example the differencing operations are performed on ECG signal samples that have been digitized at a sample rate of 250 samples per second. Thus, the result of using samples spaced 6 apart, is the HPF corner frequency of 5 Hz. In a different application, e.g., for detecting some other repetitious phenomena, a different sample spacing or filtering scheme may be preferred.

The ECG leads 4 are also applied to a QRS detector substantially of conventional design, except as to be described later, wherein in a conventional manner the amplitude of the QRS complex is calculated for each detected QRS complex on each lead 4. A separate running average (QRS AmplitudeAverage) for the QRS amplitudes is kept for each ECG lead 4.

In parallel, an artifact checker 11 is responsive to each of leads 4 for checking each lead for low frequency (LF) and high frequency (HF) artifact. Artifact checker 11 may comprise an activity checker of the type well known to those of ordinary skill in this technology, such as one that counts the frequency of amplitude excursions of the ECG signal above a predetermined threshold amplitude for determining LF and HF activity.

If no low frequency or high frequency artifact is present on a given lead, this fact is indicated to a proportional adder 10, thereby indicating that this lead is to be included by adder 10 to be combined, in accordance with the summation equation shown below, with other ones of ECG leads 4 to generate a combined (comb) signal having reduced noise which is used for QRS detection.

More specifically, proportional adder 10 operates in accordance with the following equation:

$$\text{comb }[i] = \frac{\sum_{d=1}^{N} QRS \text{ AmplitudeAverage}[j] \cdot td[i,j]}{\sum_{d=1}^{N} QRS \text{ AmplitudeAverage}[j]}$$

for adding together the QRS complexes from the various ECG signals that are determined to not have excessive LF or HF artifact.

In the above, equation, comb [i] is the i–th sample of the combined ECG signal supplied at the output of proportional adder 10; QRS AmplitudeAverage[j] is the running average of the QRS amplitude on the j–th lead (as determined by detector 14), td[i,j] is the i–th sample of the absolute value of the total difference signal on the j–th lead supplied to proportional adder 10 by HPF 8; and N is the total number of ECG leads identified by artifact detector 11 to be useable.

The result of the process implemented by the equation is a summing of the QRS complexes, for those of the N leads that are used, in accordance with their relative weight. Normalization is achieved by dividing the numerator by the sum of the running average of the QRS amplitudes on all of those of the N leads that are used. Combination of multiple ECG signals from different leads in accordance with the technique of this invention enhances the signal of the QRS complexes, thereby improving the quality of the signal for use by the QRS detector.

Initially, a running average QRS amplitude, i.e., weight, of one is assigned to the QRS complex of each lead used by adder 10. Thereafter, this weight is adapted in accordance with the determined running averages provided by QRS detector 14, so that the running average QRS amplitude applied to proportional adder 10 is always lagging the weight of the current QRS for which it is actually being used.

Next, in the preferred embodiment, the combined signal is squared before it is fed to the QRS detector. As well known, squaring of signal having both large and small components results in emphasis of the large components and de-emphasis of the small components. Additionally, in an alternative embodiment, the squared signal can be also be low pass filtered, for further reduction of any noise that may be present.

Figure 2:
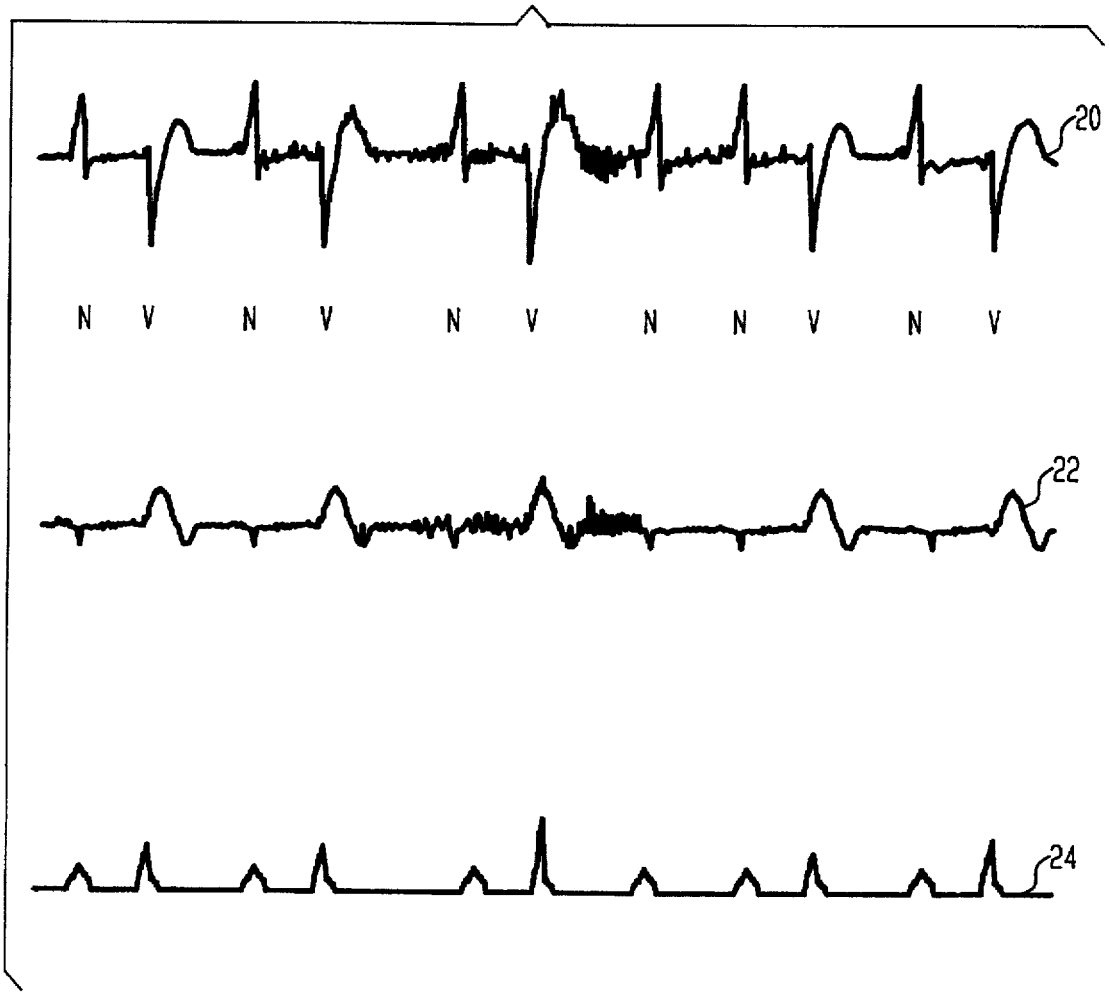
FIG. 2 illustrates waveforms useful for understanding the block diagram of FIG. 1.

The enhancement of the QRS complexes in accordance with the invention is illustrated in FIG. 2, where waveform 20 illustrates the ECG signal on lead II and waveform 22 illustrates the ECG signal on lead V. Note that significant noise is preset in these signals, and that although the QRS complexes are correlated in time, they don't have similar amplitude characteristics. Waveform 24 illustrates the squared signal provided by circuit 12 for the combination of Lead II and V. Note how "clean" the QRS's are in the squared signal, thereby greatly increasing the reliability and accuracy of the QRS detector.

Finally, the QRS detector 14 analyzes the squared comb signal for QRS detection by searching for the presence of R waves. The search for R waves is accomplished by conventional techniques, such as by looking for amplitude peaks that exceed a certain detection threshold, which threshold is dynamically adjusted according to the average timing and amplitude of previous candidates that were labeled as QRS complexes by the QRS detector. This allows the QRS detector to adjust to changes in heart rate and signal amplitude.

As is also conventional, there is a no detection, or refractory period, of 170 msecs after the identification of a QRS. During this refractory period no QRS complexes can be detected, thereby assisting in reducing the detection of T waves as R waves. After this refractory period, the QRS detection threshold decays linearly until it reaches 6% of the preceding R wave amplitude value.

The output of QRS detector 14 is then applied to the remainder 16 of the patient monitor, of conventional design, for providing a monitoring of the heart rate and arrhythmia of patient 2.

Thus, there has been shown and described a novel QRS detector arrangement which combines multiple ECG leads in accordance with the strength of their individual QRS complexes. As a result the R wave components of the QRS's are enhanced over noise because the R waves on two leads occur at the same time, while noise does not. In other words, the R waves are correlated across leads while noise may not be correlated. This enhancement results in an increased sensitivity and positive predictivity of the QRS detection. Consequently there are less false positive QRS detections, which in turn results in less false alarms. Many changes, modifications, variations and other uses and applications of the subject invention will, however, become apparent to those skilled in the art after considering this specification and the accompanying drawings which disclose a preferred embodiment thereof. For example, a repetitive signal phenomena on multiple leads other than QRS complexes could be processed in accordance with the principles of this invention, such as EEG signals, etc. Furthermore, although QRS amplitude level is used as a signal strength indicator to determine the proportional weighting of each ECG signal used to make the combined signal, a different type of signal strength indicator measurement could be used to determine the proportional weighting, such as the relative signal-to-noise ratio of each ECG signal. Additionally, other types of filtering of the multiple ECG signal or the combined output signal could be utilized. All such changes, modifications, variations and other uses and applications which do not depart from the spirit and scope of the invention are deemed to be covered by the invention which is limited only by the claims which follow.

Claims:

1. A method for reducing noise in an output signal produced from a plurality of input signals indicative of a repetitious phenomena exhibited by a signal source, said method comprising the steps of:

obtaining from a plurality of sensors positioned with respect to the signal source so as to be subjected to a unique representation of a repetitious phenomena exhibited by the signal source, a corresponding plurality of received signals in which noise may he present;

detecting the occurrence of said phenomena in each of said plurality of received signals;

determining the signal strength of said phenomena in each of said plurality of received signals; and additively combining said plurality of received signals together for developing a combined signal, with each received signal having a weight in the combined signal which is in direct proportion to the signal strength of the phenomena in that signal as determined by the prior step, the output signal indicative of said phenomena and having reduced noise being developed from said combined signal.

2. The method of claim 1, wherein said detecting step is responsive to said output signal developed by said combining step for determining timing information needed for detecting the occurrence of said phenomena in each of said plurality of received signals.

3. The method of claim 1 further including a filtering step which precedes said additive combining step for filtering each of said plurality of received signals in a frequency range which is exclusive of a given frequency range of said repetitious phenomena.

4. The method of claim 3, wherein said filtering step comprises filtering each of said received signals with a low pass filter, followed by a high pass filter.

5. The method of claim 4, wherein said low pass filter passes signals below said given frequency range and said high pass filter passes signals above said given frequency range.

6. The method according to claim 1, wherein said repetitious phenomena has a given frequency range and each of said received signals is checked for signal activity that exceeds a given threshold level in a frequency range in at least one of above and below said given frequency range, and received signal having signal activity that exceeds the given threshold level in at least one of said given frequency ranges, is not used in said additively combining step.

7. The method according to claim 1, further including the step of squaring said combined signal for developing a squared signal as said output signal, so as to enhance the amplitude of said repetitious phenomena in said output signal.

8. The method according to claim 7, wherein said detecting step comprises an amplitude detecting step, responsive to said squared signal, for detecting the occurrence of said repetitious phenomena upon detection of a signal level in said squared signal that exceeds a given amplitude threshold level.

9. The method according to claim 8, further including a step for low pass filtering of said squared signal before applying it to said amplitude detector.

10. The method according to claim 1, wherein said detecting step comprises an amplitude detecting step, responsive to said output signal, for detecting the occurrence of said repetitious phenomena upon detection of a signal level in said output signal that exceeds a given amplitude threshold level.

11. The method of claim 1, wherein said repetitious phenomena comprises a QRS complex and said signal source comprises a medical patient.

12. Apparatus for reducing noise in an output signal produced from a plurality of input signals indicative of a repetitious phenomena exhibited by a signal source, said apparatus comprising:

signal receiving means adapted for being coupled to a plurality of sensors positioned with respect to a signal source such that each of said sensors is subjected to a unique representation of a repetitious phenomena exhibited by the signal source, for obtaining from the sensors a plurality of received signals in which noise may be present;

signal detecting means for detecting the occurrence of said phenomena in each of said plurality of received signals;

signal strength determining means responsive to said plurality of received signals for determining the signal strength of said phenomena in each of said plurality of received signals; and proportional adding means responsive to said plurality of received signals and said signal strength determining means for additively combining said plurality of received signals together for developing a combined signal, with each received signal having a weight in the combined signal which is in direct proportion to the signal strength of the phenomena in that signal as determined by said signal strength determining means, the output signal indicative of said phenomena being developed from said combined signal.

13. Apparatus in accordance with claim 12, wherein said signal detecting means is responsive to said output signal developed by said proportional adding means for determining the timing for detecting the occurrence of said phenomena in each of said plurality of received signals.

\* \* \* \* \*